US010575929B2

(12) United States Patent
Fasci et al.

(10) Patent No.: US 10,575,929 B2
(45) Date of Patent: Mar. 3, 2020

(54) MULTIFORCE ORTHODONTIC ARCHWIRE

(71) Applicant: Acme Monaco Corporation, New Britain, CT (US)

(72) Inventors: Michael A. Fasci, Bristol, CT (US); Khoa Q. Tran, Bristol, CT (US); Lucas B. Karabin, Southington, CT (US)

(73) Assignee: ACME MONACO CORPORATION, New Britain, CT (US)

( * ) Notice: Subject to any disclaimer, the term of this patent is extended or adjusted under 35 U.S.C. 154(b) by 429 days.

(21) Appl. No.: 15/078,540

(22) Filed: Mar. 23, 2016

(65) Prior Publication Data
US 2016/0278883 A1    Sep. 29, 2016

Related U.S. Application Data

(60) Provisional application No. 62/137,456, filed on Mar. 24, 2015.

(51) Int. Cl.
*A61C 3/00*    (2006.01)
*A61C 7/20*    (2006.01)

(52) U.S. Cl.
CPC ..................... *A61C 7/20* (2013.01)

(58) Field of Classification Search
CPC .................... A61C 7/20; A61C 7/22
USPC ..................................... 433/18, 20
See application file for complete search history.

(56) References Cited

U.S. PATENT DOCUMENTS

| 4,197,643 | A | * | 4/1980 | Burstone | A61C 7/12 148/407 |
| 4,412,819 | A | * | 11/1983 | Cannon | A61C 7/20 433/20 |
| 4,818,226 | A | * | 4/1989 | Berendt | A61C 7/20 433/20 |
| 5,044,947 | A |   | 9/1991 | Sachdeva et al. | |
| 5,102,333 | A | * | 4/1992 | Suzuki | A61C 7/20 433/20 |
| 5,259,760 | A |   | 11/1993 | Orikasa | |

(Continued)

OTHER PUBLICATIONS

Lombardo et al., "Load Deflection Characteristics and Force Level of Nickel Titanium Initial Archwires," Angle Orthodonist, No. 3, vol. 82, 2012, published Sep. 13, 2011, p. 507-521.

(Continued)

*Primary Examiner* — Nicholas D Lucchesi
(74) *Attorney, Agent, or Firm* — Fitch, Even Tabin & Flannery, LLP (57) ABSTRACT

An orthodontic archwire includes an anterior region, bicuspids regions and posterior regions. The archwire exhibits substantially constant unloading force in at least one of the anterior region, bicuspids regions and posterior regions, having a variation of unloading force of less than 15 gf during unloading from about 2 mm to about 0.6 mm deflection. A set of orthodontic archwires can have the property that the anterior region of a first archwire has substantially the same clinical working force as the anterior region of a second archwire, the bicuspids regions of the first archwire has substantially the same clinical working force as the bicuspids regions of the second archwire, and the posterior regions of the first archwire has substantially the same clinical working force as the posterior regions of the second archwire.

7 Claims, 6 Drawing Sheets

(56) References Cited

U.S. PATENT DOCUMENTS

| | | | | | |
|---|---|---|---|---|---|
| 5,588,833 | A | * | 12/1996 | Risse | A61C 7/20 |
| | | | | | 433/20 |
| 5,683,245 | A | | 11/1997 | Sachdeva et al. | |
| 6,132,209 | A | * | 10/2000 | Devanathan | C22C 14/00 |
| | | | | | 433/20 |
| 6,375,458 | B1 | * | 4/2002 | Moorleghem | A61B 17/866 |
| | | | | | 433/2 |
| 6,431,861 | B1 | * | 8/2002 | White | A61C 7/20 |
| | | | | | 433/20 |
| 7,455,737 | B2 | * | 11/2008 | Boismier | C22F 1/006 |
| | | | | | 148/402 |
| 2002/0172910 | A1 | * | 11/2002 | Bond | A61C 7/20 |
| | | | | | 433/20 |
| 2015/0072299 | A1 | * | 3/2015 | Alauddin | A61C 7/141 |
| | | | | | 433/20 |

OTHER PUBLICATIONS

Letter from third party dated Apr. 12, 2017 and in the office of the undersigned.
Claim Chart in the office of the undersigned from a third party.
Compositions Comparison Chart in the office of the undersigned from a third party.

* cited by examiner

MULTIFORCE ORTHODONTIC ARCHWIRE

CROSS-REFERENCE TO RELATED APPLICATION

This application is a nonprovisional application of and claims benefit of the filing date of provisional application No. 62/137,456, filed Mar. 24, 2015.

BACKGROUND OF THE INVENTION

The present invention generally relates to appliances used in orthodontics and more specifically to orthodontic archwires used to provide forces to correct malocclusions between the teeth in the dental arch.

An orthodontic archwire is provided to apply corrective clinical forces to a patient's dental arch. The orthodontic archwire with a single or multi curved plane fits into orthodontic appliances such as brackets which are applied to the patient's teeth. The archwire material will generally be supplied in a round, square, or rectangular cross-section. A preformed archwire shape is selected for use based on the optimal dental arch shape for the patient being treated. When the preformed archwire is engaged in a patient with malocclusions in the dental arch, forces are applied to the orthodontic appliances to align and level the patient's teeth into the planned dental arch.

Figure 1A:
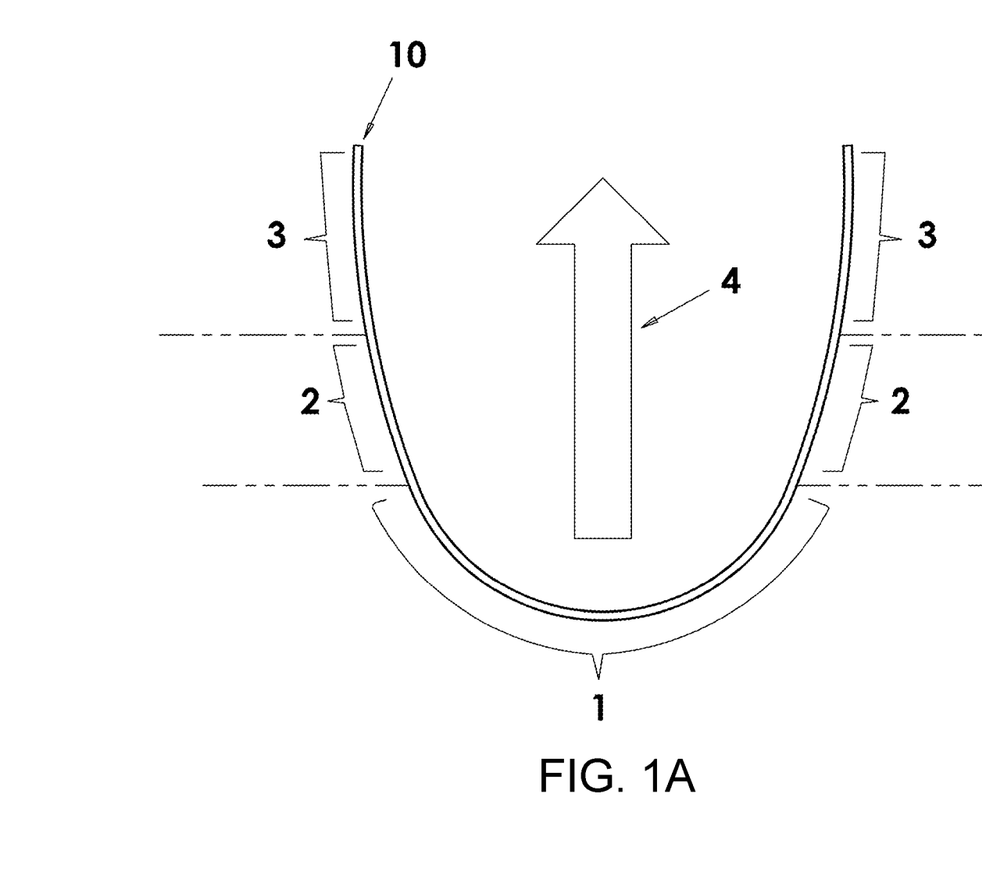
FIGS. 1A and 1B depict, in plan and perspective views, respectively, a preformed archwire shape and the three sections of the archwire.
Figure 1B:
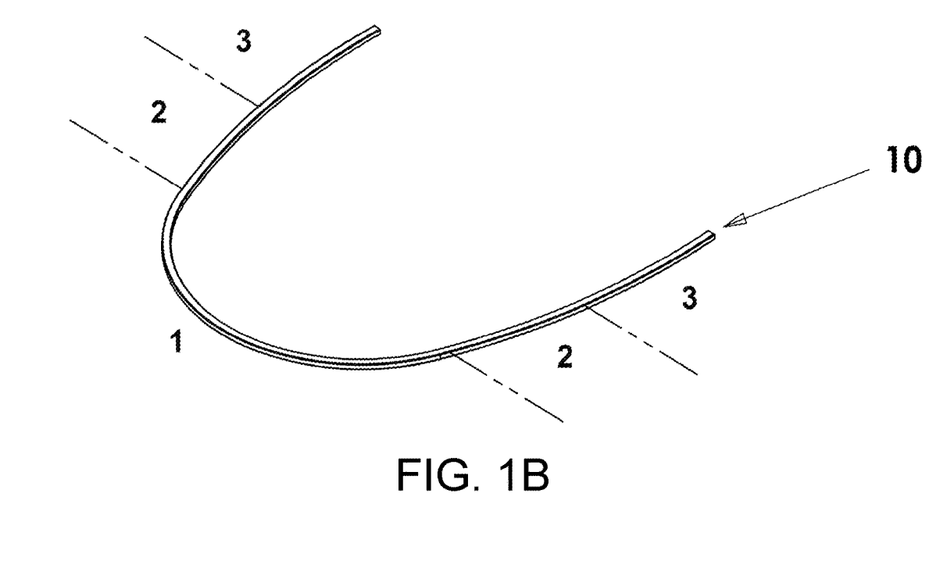
Figure 1C:
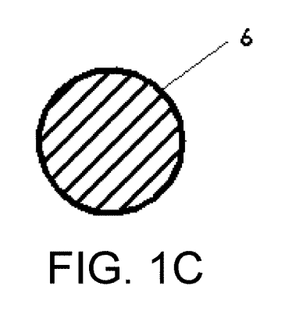
FIGS. 1C, 1D and 1E show three typical archwire cross-sections, i.e., respectively, round, square and rectangular cross-sections.
Figure 1D:
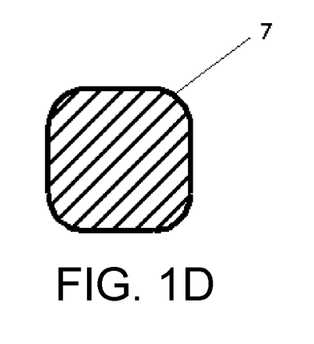
Figure 1E:
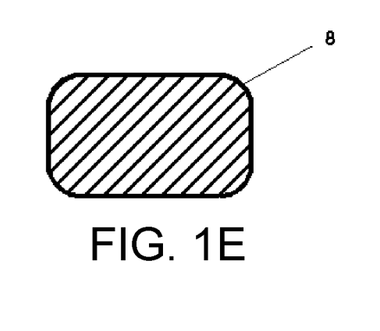

FIGS. 1A and 1B depict, in plan and perspective views, respectively, a preformed archwire shape 10 and the three sections of the archwire with incremental increases in force 4 within the three distinct areas—anterior teeth 1 (the centrals, laterals, and cuspids; i.e., the teeth in the front of the dental arch), bicuspids 2 (the first and second bicuspids; i.e., the teeth between the cuspids and molars), and posterior teeth 3 (the molars; i.e., the teeth in the back of the dental arch). FIGS. 1C, 1D and 1E show three typical archwire cross-sections, i.e., respectively, round 6, square 7 and rectangular 8 cross-sections.

In orthodontics, various appliances are used to correct malocclusions of the teeth. During the treatment cycle, it is quite often necessary to impart forces on the teeth to move the teeth into their desired location. This movement of the teeth is generally treated through a combination of appliances with one of the most important being the orthodontic archwire. The orthodontic archwire is secured within brackets which are mounted onto a patient's teeth. Prior art orthodontic archwires have been limited in respect to their ability to provide optimal clinical forces and corrective measures to all areas within the dental arch simultaneously. The result is many sequencing of wires to engage certain teeth and not others or concerns that the necessary forces required for larger teeth may impact the health of the smaller ones.

U.S. Pat. No. 5,044,947 to Sachdeva et al. is an attempt to provide an orthodontic appliance made of a shape memory alloy comprising of a nickel, titanium, and copper composition which is formulated to provide the desired loading and unloading forces to the bracket.

U.S. Pat. No. 5,683,245 to Sachdeva et al. discloses an archwire made of a shape memory alloy having a preset shape for exerting forces on teeth during orthodontic treatment. The alloy, which preferably is comprised of at least three elements (e.g., Ni, Ti and Cu), has a transformation temperature ($A_f$) greater than about 25° C., whereby the orthodontic archwire produces forces at normal mouth temperature which are greater than the forces produced at normal room temperature. The orthodontic archwire also preferably has a variable modulus of elasticity.

U.S. Pat. No. 5,259,760 to Orikasa also discloses an orthodontic arch wire capable of exerting forces on the dental arch that gradually vary in magnitude along the wire.

SUMMARY OF THE INVENTION

In one aspect of the present invention, an orthodontic archwire includes an anterior region, bicuspids regions and posterior regions. The archwire exhibits substantially constant unloading force in at least one of the anterior region, bicuspids regions and posterior regions, having a variation of unloading force of less than 15 gf during unloading from about 2 mm to about 0.6 mm deflection.

The orthodontic archwire may exhibit substantially constant unloading force in each of the anterior region, bicuspids regions and posterior regions, having a variation of unloading force of less than 15 gf during unloading from about 2 mm to about 0.6 mm deflection.

The orthodontic archwire may be made from an alloy comprising copper, nickel and titanium.

The orthodontic archwire may be made from an alloy comprising 4 to 8% by weight copper, 47 to 50% nickel and 44 to 47% titanium.

The orthodontic archwire may be made from an alloy comprising copper, nickel, titanium and chromium.

The orthodontic archwire may be made from an alloy comprising 47 to 50% by weight nickel, 44 to 47% by weight titanium, 4 to 8% by weight copper and 0.1 to 0.5% by weight chromium.

In another aspect of the present invention, a set of orthodontic archwires comprising a first arch wire having an anterior region, bicuspids regions and posterior regions, and a second arch wire having an anterior region, bicuspids regions and posterior regions, the first arch wire having a different cross-sectional shape or a different cross-sectional size than the second archwire, wherein the anterior region of the first archwire has substantially the same clinical working force as the anterior region of the second archwire, the bicuspids regions of the first archwire have substantially the same clinical working force as the bicuspids regions of the second archwire, and the posterior regions of the first archwire have substantially the same clinical working force as the posterior regions of the second archwire.

The orthodontic archwire may be made from an alloy comprising copper, nickel and titanium.

The orthodontic archwire may be made from an alloy comprising 4 to 8% by weight copper, 47 to 50% nickel and 44 to 47% titanium.

The orthodontic archwire may be made from an alloy comprising copper, nickel, titanium and chromium.

The orthodontic archwire may be made from an alloy comprising 47 to 50% by weight nickel, 44 to 47% by weight titanium, 4 to 8% by weight copper and 0.1 to 0.5% by weight chromium.

DESCRIPTION OF THE INVENTION

Despite the archwires described in the Sachdeva et al. patents and in the Orikasa patent, it would still be desirable to provide an archwire having a more constant clinical working force or unloading force (i.e., the clinical force a wire exerts after the wire is installed in the appliances attached to the patient's teeth) in each section and a more constant clinical working force in each section independent of the cross-sectional size.

The present invention is directed to orthodontic archwires which provide optimal tooth moving forces at appropriate regions within the dental arch.

The invention incorporates the unique ability of providing comparable tooth movement forces even when a different material size or cross-section is selected by the orthodontist due to the unique case he/she is working on.

The present invention includes many archform shapes and material sizes to address the variety of orthodontic cases.

In a preferred embodiment, the archwire of the present invention is a "multi-force archwire," i.e., an archwire that exhibits different clinical working forces in a plurality, e.g., three or more distinct regions along the orthodontic archwire. This is also known as variable force archwire.

By combining copper with a nickel titanium alloy in appropriate amounts, benefits are achieved by reducing the differential between in the loading (engaging) and unloading (working) forces. This reduction in span between the loading and unloading force curves provides benefits such as lower patient discomfort. Other benefits from the blend of alloys include a more constant working force, consistent $A_f$ temperature, and a greater duration of optimal forces from the patient loading to fully recovered state.

The copper nickel titanium alloy used for the archwire of the present invention has a transformation temperature ($A_f$) equal to or greater than 24° C. which allows the wire to be in the martensitic or "soft" phase at room temperature, and turns austenitic with a higher exerted force when placed into the oral cavity.

The forces produced by the archwire at body temperature (approximately 37° C.) are at least 15% greater than the forces produced at room temperature (20° C.).

The average unloading force regardless of material cross section or area is preferably about 35 to 80 grams on the anteriors, about 80 to 130 grams on the bicuspids, and 130 to 200 grams on the posteriors, more preferably about 50 grams on the anteriors, about 100 grams on the bicuspids, and 150 grams on the posteriors. See ORTHODONTICS—Prep Manual for Undergraduates by Sridhar Premkumar, Elsevier, the content of which is incorporated herein in its entireties, for discussion of optimal tooth movement forces.

The composition of the alloy used for the archwire of the present invention includes at least three elements, and the composition of each is in an amount of 3% or greater by weight.

The composition of the alloy used for the archwire of the present invention preferably includes nickel, titanium, and copper in amounts of 47 to 50% by weight nickel, 44 to 47% by weight titanium and 4 to 8% by weight copper, more preferably about 49% nickel by weight, 45.1% titanium by weight, and about 5.9% of copper by weight. The composition may include nickel, titanium, copper, and chromium, in which case, the composition preferably includes 47 to 50% by weight nickel, 44 to 47% by weight titanium, 4 to 8% by weight copper and 0.1 to 0.5% by weight chromium, more preferably about 49% nickel, about 44.8% titanium, 5.9% copper, and 0.3% chromium. The term "about" is used to reflect that the alloy may contain incidental impurities or trace elements. Generally, incidental impurities or trace elements may be contained in an amount of up to 0.4% by weight.

The application of continuous force applied to a tooth surface results in remodeling of the alveolar bone, reorganization of the periodontal ligament, and resulting tooth movement. The magnitude of force is very important as high force levels that exceed the capillary pressure within the periodontal ligament can cause a restriction of blood supply to the tissues, tissue injury, and premature cell death in the tissues.

The typical archwire used in orthodontics is constructed of a material with a single structural force along the entire archwire length. This characteristic provides significant challenges to the orthodontist as forces appropriate for the posterior teeth are far too strong for the anterior and light forces applied to the anterior may have no tooth movement effect of posteriors.

To address these issues, the archwire of the present invention provides the following benefits:

Ideal clinical forces are provided in each of the three regions within the dental arch. Light forces are applied to the anterior teeth, mid-range force to the bicuspids, and stronger forces for the posterior teeth.

The addition of the copper element in the material reduces the differential between the loading (wire engaging) and unloading (clinical working) force curves which improves the ease of wire engagement for cases with moderate to severe tooth misalignment. Other benefits such as less patient discomfort and more consistent tooth movement as a result of the wire maintain a longer active force in the optimal force range.

The archwire of the present invention can provide the optimal force to the three regions in the dental archwire even when the orthodontist requires a different wire size and/or material cross section. As an example, based on the needs for the particular case, the orthodontist can apply a 0.016" round wire or a 0.017"× 0.025" rectangular wire, and the two parts will supply equivalent forces in each region of the dental arch. Prior to this invention, as the material size or cross section increases, the forces provided by the wire will typically increase. Smaller the cross section, lower the force, larger the cross section, higher the force.

In the present invention the orthodontic archwires are thermally processed to achieve the desired force characteristics (modulus of elasticity) along the archwire length. Subsequent thermal processing of the archwire may be performed to provide desired force characteristics (modulus of elasticity) at specific zones within the dental arch such as the anteriors, bicuspids, and posterior teeth. The method of thermal processing includes automated product movement in the zone areas to prevent any unfavorable material conditions within zone transitions that may have a detrimental effect on clinical performance.

In one method of the present invention, the entire archwire would be thermally processed to the proper force (modulus of elasticity) for the zone which includes the posterior teeth. This thermal processing would consist of a heat treatment of about 350° C. to 575° C. for about 5 minutes to 60 minutes. Subsequent thermal processing will be performed to achieve the desired force at the bicuspids, and anterior zones with heat treatments of about 350° C. to 575° C. for about 5 minutes to 60 minutes in each of these zones.

The advantageous properties of the archwire of the present invention will become apparent from the data described hereinafter.

Figure 2:
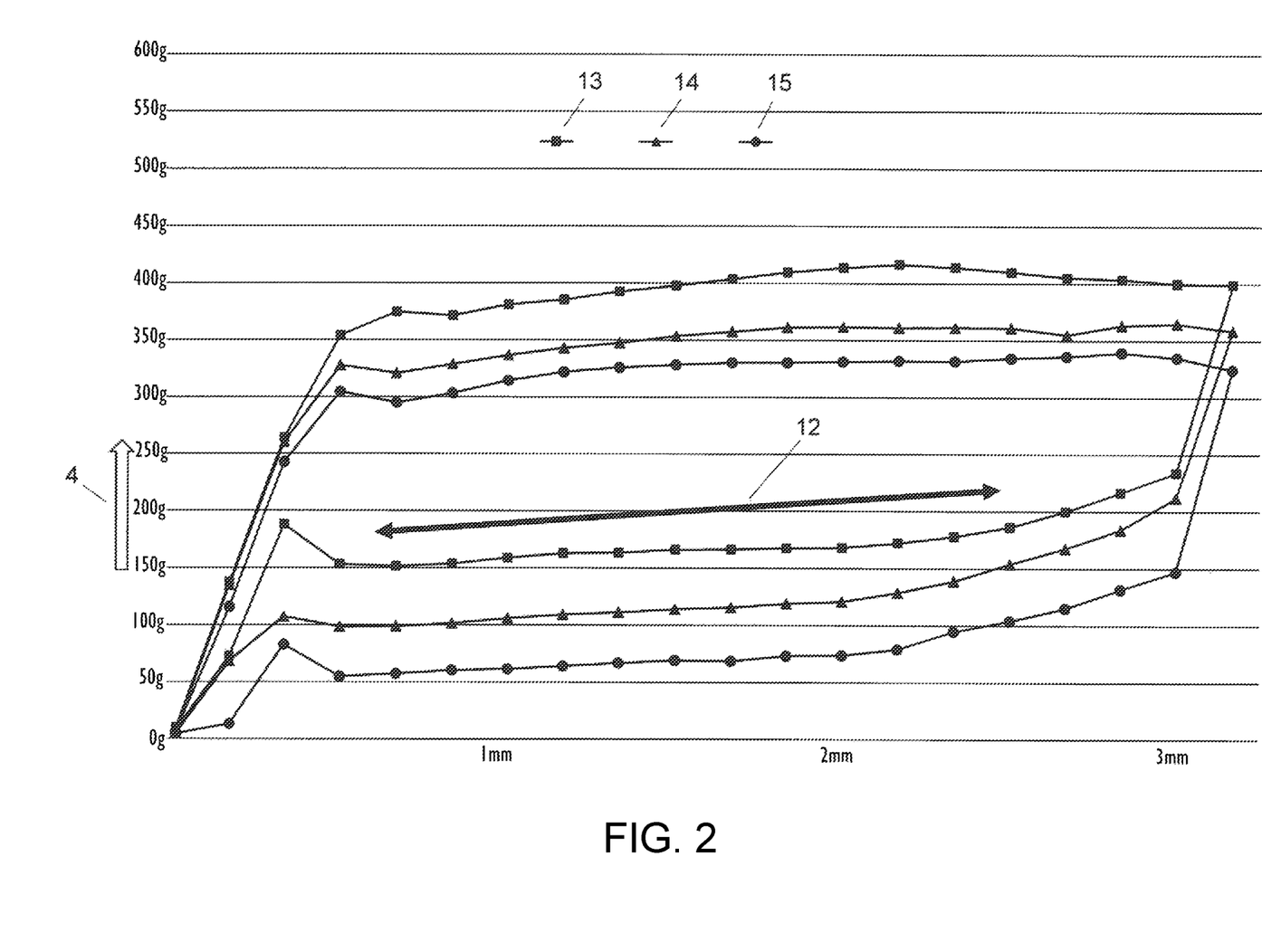
FIG. 2 shows the results of testing a 0.016"×0.022" rectangular cross-section "Bioforce" nickel titanium wire from Tomy K.K. of Tokyo, Japan by the 3 point bend test per ISO 15841.

FIG. 2 shows the results of testing a 0.016"×0.022" rectangular cross-section "Bioforce" nickel titanium wire from Tomy K.K. of Tokyo, Japan by the 3 point bend test per ISO 15841. ISO 15841 is an International Standard for the testing of wires for orthodontic use (titled: "Dentistry— Wires for use in orthodontics"). As can be seen from FIG. 2, which shows the load (gf) plotted against the deflection (mm) during loading and unloading, the archwire has variable forces at select areas of the archwire (posteriors, bicuspids and anteriors). However, as shown in FIG. 2, the force is not constant during unloading in any of the posteriors (curve 13), bicuspids (curve 14) and anteriors (curve 15) regions of the archwire. For example, in the posterior region, the force varies from about 170 gf at about 2 mm deflection to about 150 gf at about 0.6 mm deflection. Similar variations are present in the bicuspid and anterior regions. The double-headed arrow 12 above the unloading curve depicts the drop in force as the wire returns from a deflection of 3 mm to the 0 mm origin.

Thus, the "Bioforce" nickel titanium wire from Tomy K.K. fails to provide sufficiently constant unloading forces.

Figure 3:
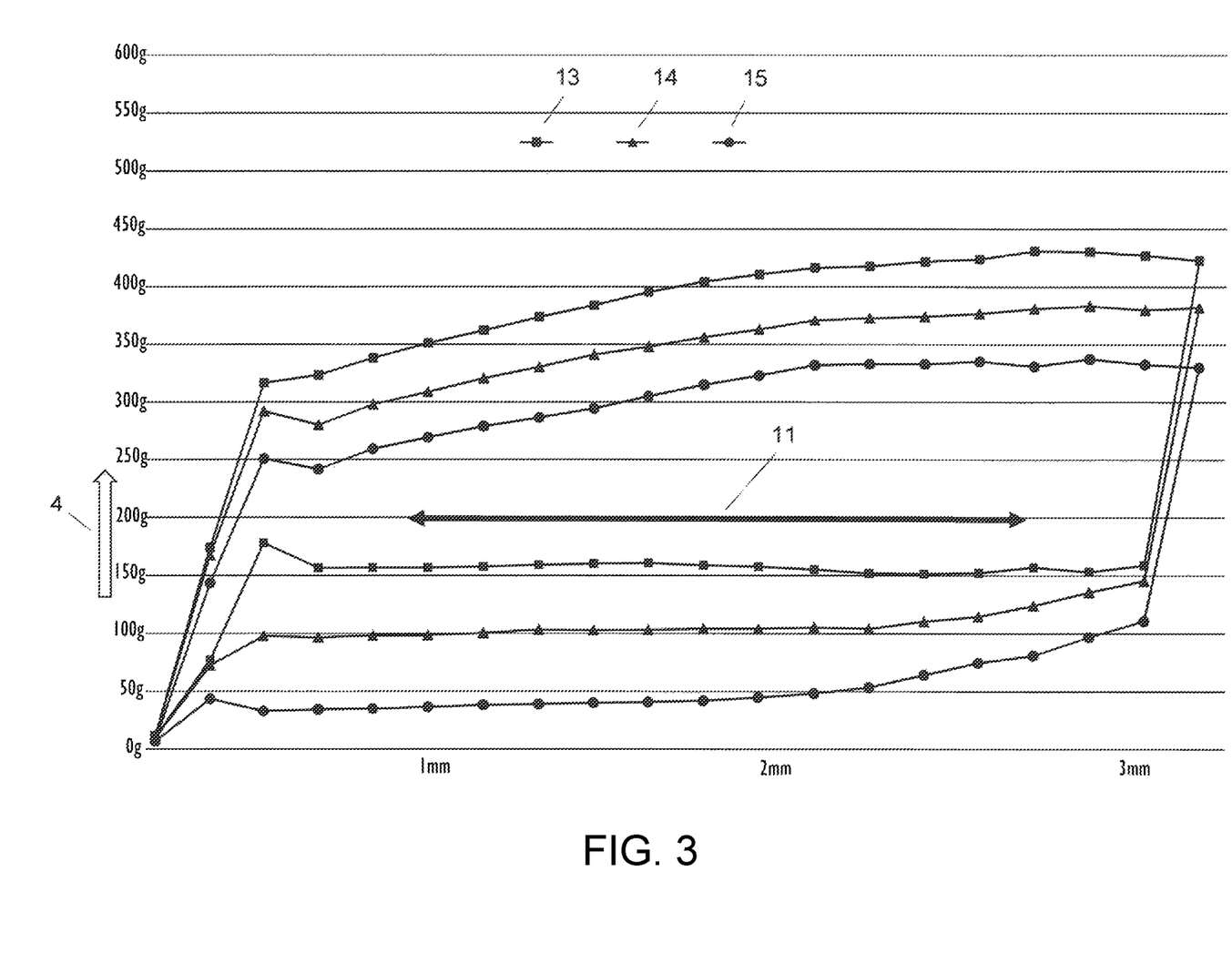
FIG. 3 shows the results of testing a 0.016"×0.022" rectangular cross-section multi-force copper nickel titanium archwire of the present invention using the 3 point bend test per ISO 15841.

On the other hand, as shown in FIG. 3, when testing a 0.016"×0.022" rectangular cross-section multi-force copper nickel titanium archwire of the present invention (about 49.1% by weight nickel and 44.7% by weight titanium, 5.9% by weight copper, 0.3% chromium) using the 3 point bend test per ISO 15841, the results show substantially constant unloading force (double headed arrow 11) of the copper nickel titanium material blend promoting more uniform tooth movement and malocclusion correction. By substantially constant unloading force is meant a variation of unloading force of less than 15 gf during unloading from about 2 mm to about 0.6 mm deflection. Preferably, the variation of unloading force is less than 5 g in the posterior section (curve 13), 10 g in the bicuspid region (curve 14) and 15 grams in the anterior region (curve 15) during unloading from about 2 mm to about 0.6 mm deflection, or in percentage of variation, preferably less than 20% on the anterior region, 15% on the Mid or Bicuspid region, and 10% on the posterior region.

Thus, it can be seen that the multi-force copper nickel titanium wire of the present invention provides a longer duration of constant tooth movement forces, which will result in a higher level of wire efficiency. The multi-force copper nickel titanium wire of the present invention also provides three distinct wire force regions with optimal forces for each region of the patient's dental arch.

Figure 4:
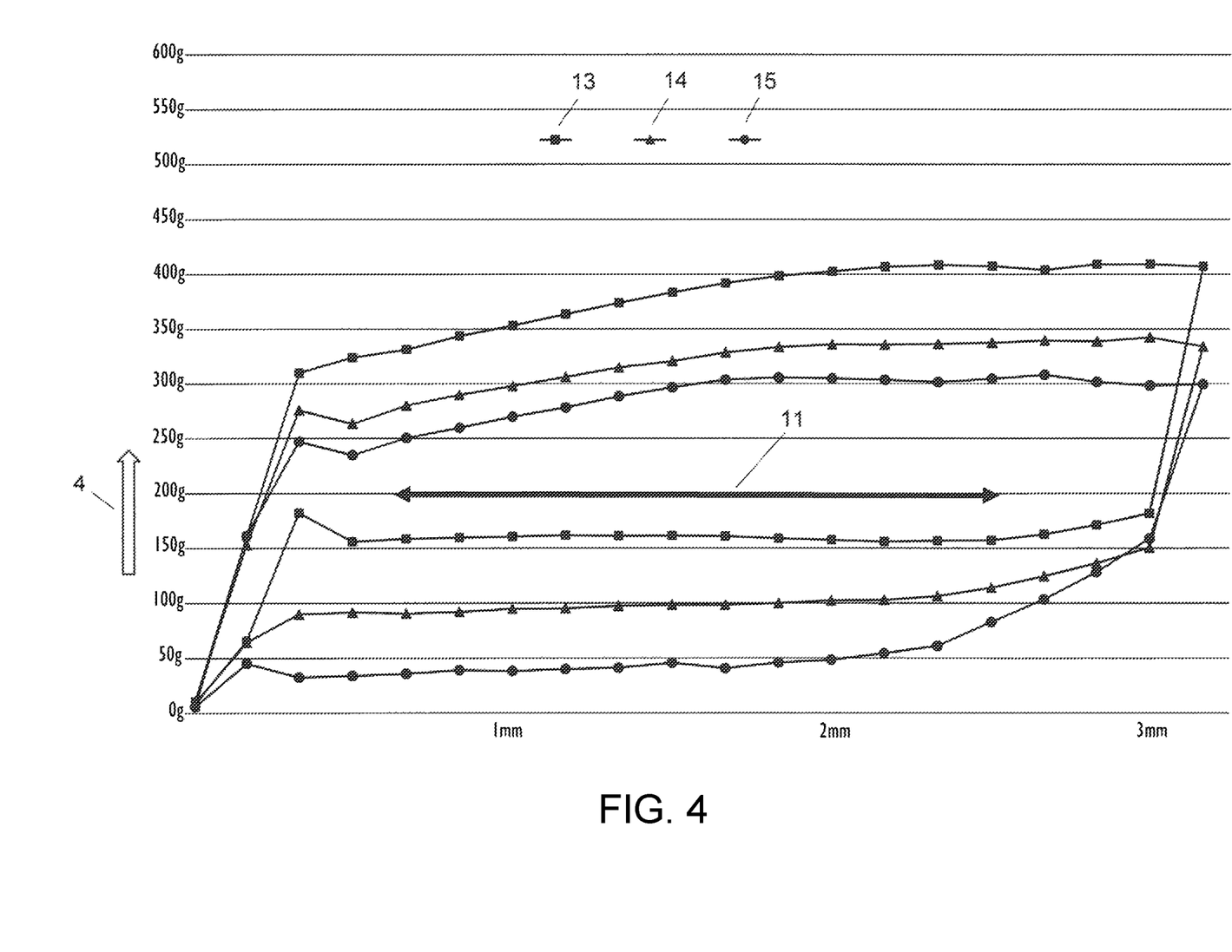
FIG. 4 shows the results of testing a 0.018" round cross-section multi-force copper nickel titanium archwire of the present invention using the 3 point bend test per ISO 15841.

FIG. 4 shows the results of testing a 0.018" round cross-section multi-force copper nickel titanium archwire of the present invention (about 49.3% by weight nickel and 44.2% by weight titanium, 6.2% by weight copper, 0.3% chromium,) using the 3 point bend test per ISO 15841. The results are similar to those in FIG. 3 and show substantially constant unloading force (double headed arrow 11) of the copper nickel titanium material blend promoting more uniform tooth movement and malocclusion correction.

By comparing FIGS. 3 and 4, it can be seen that two distinctly different cross-section archwires of the present invention, a 0.016"×0.022" rectangular wire archwire (FIG. 3) and a 0.018" round wire archwire (FIG. 4) provides the substantially the same clinical forces (less than 5% difference in each region) required to promote optimal tooth movement. The benefit of this invention is that it enables the orthodontist to utilize the wire cross section of choice based on the clinical case, and still provide the optimal tooth movement forces. An example would be engaging a larger cross sectional wire size earlier in the treatment cycle to fill the bracket slot and perform leveling and aligning simultaneously.

The invention claimed is:

1. A set of orthodontic archwires comprising a first arch wire having an anterior region, bicuspids regions and posterior regions, and a second arch wire having an anterior region, bicuspids regions and posterior regions, the first arch wire having a different cross-sectional shape or a different cross-sectional size than the second archwire, wherein the anterior region of the first archwire has substantially the same clinical working force as the anterior region of the second archwire, the bicuspids regions of the first archwire have substantially the same clinical working force as the bicuspids regions of the second archwire, and the posterior regions of the first archwire have substantially the same clinical working force as the posterior regions of the second archwire.

2. The set of orthodontic archwires according to claim 1, wherein each of the first and second archwires is made from an alloy comprising copper, nickel and titanium.

3. The set of orthodontic archwires according to claim 2, wherein the alloy comprises 4 to 8% by weight copper, 47 to 50% nickel and 44 to 47% titanium.

4. The set of orthodontic archwires according to claim 1, wherein each of the first and second archwires is made from an alloy comprising copper, nickel, titanium and chromium.

5. The set of orthodontic archwires according to claim 4, wherein the alloy comprises 47 to 50% by weight nickel, 44 to 47% by weight titanium, 4 to 8% by weight copper and 0.1 to 0.5% by weight chromium.

6. The orthodontic archwire according to claim 1, wherein the first arch wire has a different cross-sectional size than the second archwire.

7. The orthodontic archwire according to claim 1, wherein the first arch wire has a different cross-sectional shape and a different cross-sectional size than the second archwire.

* * * * *